(12) United States Patent
Williams et al.

(10) Patent No.: US 7,799,966 B2
(45) Date of Patent: *Sep. 21, 2010

(54) FIBROUS ABSORBENT ARTICLES HAVING MALODOR COUNTERACTANT ABILITY AND METHOD OF MAKING SAME

(75) Inventors: Karla E. Williams, Westwood, NJ (US); Rosemary F. Knuth, Congers, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/832,709

(22) Filed: Apr. 11, 2001

(65) Prior Publication Data

US 2002/0010447 A1 Jan. 24, 2002

(51) Int. Cl.
*A61F 13/15* (2006.01)

(52) U.S. Cl. .................. 604/359; 604/360; 604/385.17; 604/375; 604/904

(58) Field of Classification Search .................. 604/359, 604/360, 375, 904, 385.17, 385.18; 424/76.1–76.4
See application file for complete search history.

(56) References Cited

U.S. PATENT DOCUMENTS

| 2,024,145 A | 12/1935 | Cline ........................... 167/84 |
| 3,585,998 A | 6/1971 | Hayford et al. ............. 128/284 |
| 3,690,321 A * | 9/1972 | Hirschman et al. .......... 604/359 |
| 3,732,867 A | 5/1973 | Money .................. 128/290 R |
| 3,830,237 A * | 8/1974 | Bernardin et al. ........... 604/359 |
| 3,948,257 A | 4/1976 | Bossak ........................ 128/285 |
| 4,525,410 A | 6/1985 | Hagiwara et al. ............. 428/198 |
| 4,583,980 A | 4/1986 | Schneider et al. ........... 604/359 |
| 4,722,936 A * | 2/1988 | Jacob ......................... 514/474 |
| 4,748,978 A | 6/1988 | Kamp ........................ 128/156 |
| 4,795,482 A | 1/1989 | Gioffre et al. ................... 55/75 |
| 4,826,497 A | 5/1989 | Marcus et al. .............. 604/359 |
| 4,880,417 A | 11/1989 | Yabrov et al. ............... 604/355 |
| 4,911,898 A | 3/1990 | Hagiwara et al. ........... 423/118 |
| 4,911,899 A | 3/1990 | Hagiwara et al. ........... 423/118 |
| 4,985,023 A | 1/1991 | Blank et al. ................. 604/360 |
| 5,019,062 A | 5/1991 | Ryan et al. ................... 604/359 |
| 5,037,412 A | 8/1991 | Tanzer et al. ................ 604/359 |
| 5,122,407 A | 6/1992 | Yeo et al. .................... 428/138 |
| 5,290,268 A | 3/1994 | Oliver et al. ................ 604/359 |
| 5,306,487 A | 4/1994 | Karapasha et al. ......... 424/76.6 |

(Continued)

FOREIGN PATENT DOCUMENTS

DE 2024930 12/1971

(Continued)

OTHER PUBLICATIONS

Supplemental European Search Report for EP 01 92 6938 dated Apr. 2, 2008.

*Primary Examiner*—Jacqueline F. Stephens
(74) *Attorney, Agent, or Firm*—Ohlandt, Greeley, Ruggiero & Perle, L.L.P.

(57) ABSTRACT

There is provided a fibrous absorbent article for absorbing body fluids. The article includes a fibrous absorbent material suitable for absorbing the body fluids, and one or more all-natural, liquid malodor counteractant materials disposed within the fibrous material to absorb, neutralize, suppress, and/or eliminate odors associated with the body fluids. The one or more malodor counteractant materials is one or more of the following: glycerin, glycerin compound, aldehyde, natural oil, solution of soluble natural compound, natural plant and herb extract, naturally occurring deodorizing active, acid, base, oxidant, chelating agent, ester, masking agent, sensory receptor alterant, oxidizing agent, biological agent, surfactant, surface active polymer, and any mixtures thereof.

13 Claims, 3 Drawing Sheets

U.S. PATENT DOCUMENTS

| | | | |
|---|---|---|---|
| 5,342,333 A | 8/1994 | Tanzer et al. | 604/359 |
| 5,364,380 A | 11/1994 | Tanzer et al. | 604/359 |
| 5,407,442 A | 4/1995 | Karapasha | 604/359 |
| 5,417,224 A * | 5/1995 | Petrus et al. | 128/933 |
| 5,429,628 A | 7/1995 | Trinh et al. | 604/359 |
| H1579 H | 8/1996 | Furio | 502/402 |
| 5,733,272 A | 3/1998 | Brunner et al. | 604/359 |
| H1732 H | 6/1998 | Johnson | 428/68 |
| 5,769,832 A | 6/1998 | Hasse | 604/359 |
| 5,769,833 A | 6/1998 | Hasse | 604/359 |
| 5,817,300 A | 10/1998 | Cook et al. | 424/66 |
| 5,944,704 A | 8/1999 | Guarracino et al. | 604/359 |
| 5,944,933 A | 8/1999 | Heller et al. | 156/276 |
| 6,031,043 A * | 2/2000 | Dupuis et al. | 524/603 |
| 6,635,205 B2 * | 10/2003 | Williams et al. | 264/103 |
| 2003/0093043 A1 * | 5/2003 | Yi et al. | 604/359 |

FOREIGN PATENT DOCUMENTS

| | | |
|---|---|---|
| EP | 813848 A1 * | 12/1997 |
| FR | 2 747 310 | 10/1997 |
| WO | WO 99/64083 | 12/1999 |
| WO | WO 00/65911 | 11/2000 |
| WO | WO 00/67688 | 11/2000 |

\* cited by examiner

| Glycerin Data | |
|---:|---:|
| | |
| | |
| 0.005 | 53.09 |
| 0.01 | 73.2 |
| 0.025 | 83.21 |
| 0.05 | 92.6 |
| 0.1 | 95.15 |
| | |
| grams | % Efficacy |
| | |
| | |
| | |
| | |
| | |
| | |

FIG. 3

FIBROUS ABSORBENT ARTICLES HAVING MALODOR COUNTERACTANT ABILITY AND METHOD OF MAKING SAME

BACKGROUND OF THE INVENTION

1. Field of the Invention

The present invention relates to fibrous absorbent articles, such as tampons and other catamenial devices, intended for absorption of body fluids. Such fibrous articles include one or more malodor counteractant materials for the purpose of absorption, suppression, neutralization, and/or elimination of menstrual malodors. The one or more malodor counteractant materials may be naturally sourced and may be in liquid form for ease and uniformity of application.

Fibrous absorbent articles have been known for some time. They incorporate a plurality of fibers arranged in a structure to absorb and retain body fluids. In connection with the present invention, the body fluid of particular concern is menstrual fluid that may generate unpleasant odors.

A variety of proposals have been made in the past as a way to counteract menstrual odors. Such proposals include the use of perfumes to mask the odors that emanate from the absorbent article. Other proposals include the use of substances to suppress or remove odoriferous compounds that may be generated in the presence of menstrual fluids and the like. These odoriferous compounds may be suppressed by a number of mechanisms including forming a non-odoriferous compound by chemical reaction or by absorption of the odoriferous compounds into a solid or liquid. For an absorbent to be effective in deodorizing, especially for odors from body fluids that are characterized as having very low olfactory thresholds, it is essential that the sorbent be capable of removing, in its environment, virtually all the odoriferous compounds regardless of the concentration thereof.

2. Description of the Prior Art

In order to provide a full background for the present invention reference may be made to U.S. Pat. Nos. 3,948,257; 4,795,482; 4,826,497; and 5,364,380; also Registration HI579.

U.S. Pat. No. 3,948,257 is directed to a vulva deodorant system comprising a tampon for insertion into the vagina and a device for retaining a deodorant. The device includes a deodorant in the form of a perfume, powder or the like.

U.S. Pat. No. 4,795,482 is directed to a process for eliminating odors and compositions for use therein. The method involves reducing the odors below olfactory detection by contact of the odor producing species with a synthetic crystalline siliceous molecular sieve material.

U.S. Pat. No. 4,826,497 provides fibrous absorption articles having enhanced deodorizing properties by having disposed therein an effective amount of crystalline siliceous molecular sieve having pore diameters of at least about 5.5 Angstroms and a relatively low capacity for adsorbed water. In addition, this patent provides for the inclusion of zeolite particles having a size of less than about 20 micrometers in the deodorizing sieve. The particles are positioned between the exterior surface of the fluid permeable cover of the absorbent article and a baffle provided within the article.

U.S. Pat. No. 5,364,380 provides an absorbent article having a first surface facing the body of a user and a second surface aligned approximately opposite to the first surface. There is also provided a liquid-impermeable baffle and a fluid-permeable cover positioned adjacent to the respective surfaces. In addition, a deodorizing mixture is positioned in the article to remain dry for a substantial period of time. The mixture is an anhydrous, non-buffer blend of at least basic and pH neutral odor adsorbing particles.

Registration HI579 provides zeolites having "intermediate" $SiO_2/Al_2O_3$ ratios used in catamenials, diapers and the like to control odors. Such intermediate ratios are described as typically in the range from about 2 to about 10.

It may be the case that when applied appropriately there are particular benefits and advantages to the several inventions described in the aforesaid patents. However, it will be apparent that the present invention provides a key advantage not found in prior art. What has been discovered and recognized is that the one or more malodor counteractant materials of the present invention have the capacity to absorb odiferous organic molecules and, in addition, lower vapor pressure, which in turn, has the property of controlling and suppressing odor. Consequently, a very effective and efficacious fibrous absorbent article, for example, a tampon, can be fabricated in such a way as to capitalize on the one or more malodor counteractant material's capability of absorbing odiferous organic molecules associated with menstrual fluids to lower the vapor pressure and therefore lower the threshold of the odiferous materials. This is achieved even in the presence of water that may be present in such fluids.

SUMMARY OF THE INVENTION

It is an object of the present invention to provide a fibrous absorbent catamenial article or product, such as a tampon, that can be reliably and inexpensively produced and that will efficiently absorb odors associated with menstrual fluid.

It is another object of the present invention to provide such a tampon having one or more malodor counteractant materials.

It is yet another object of the present invention to provide such a tampon where the one or more malodor counteractant materials are naturally sourced.

It is still another object of the present invention to provide such a tampon where the one or more malodor counteractant materials are in liquid form.

It is a further object of the present invention to maximize the effect of a desired amount of the one or more malodor counteractant materials in a tampon.

It is still a further object of the present invention to provide the tampon with efficient odor absorption even in the presence of water or other liquid.

It is yet a further object of the present invention to provide a method of incorporating the one or more malodor counteractant materials into a tampon.

It is another object of the present invention to provide such a tampon having one or more malodor counteractant materials that will not support microbial growth.

The above and other objects and advantages of the present invention are achieved by a tampon or similar device or product in which there is disposed one or more, natural sourced, malodor counteractant materials. Briefly stated, a broad feature of the present invention is a fibrous absorbent article for absorbing body fluids made up of a fibrous material defining a structure suitable for absorbing the body fluids, and disposed within the structure an effective amount of one or more malodor counteractant materials, so as to absorb, neutralize, suppress, and/or eliminate odors associated with these bodily fluids. In one preferred embodiment, the malodor counteractant material is glycerin. In an even more preferred form of this embodiment, the glycerin is in liquid form. In yet an even more preferred embodiment, the liquid glycerin is all naturally sourced. In a second embodiment, the malodor counteractant material includes glycerin in combination with one or more additional malodor counteractant materials, the combination of which further counteracts malodor.

Other and further objects, advantages and features of the present invention will be understood by reference to the following specification in conjunction with the annexed drawings, wherein like parts have been given like numbers.

DESCRIPTION OF THE INVENTION

The present invention is directed to fibrous devices, such as tampons and other catamenial devices, having one or more malodor counteractant materials. The malodor counteractant materials are derived from all natural sources and are in liquid form. Moreover, the malodor counteractant materials do not support microbial growth.

The one or more malodor counteractant materials can be any suitable materials capable of absorbing, suppressing, neutralizing, and/or eliminating malodors emanating from body fluids, such as, for example, menstrual fluid. Suitable malodor counteractant materials include, for example, one or more glycerins, glycerin compounds, aldehydes, natural oils, solutions of soluble natural compounds, natural plant and herb extracts, naturally occurring deodorizing actives, acids, bases, oxidants, chelating agents, esters, masking agents, sensory receptor alterants, oxidizing agents, biological agents, surfactants, surface active polymers, or any mixtures thereof.

Suitable glycerin compounds for use in the present invention include, for example, glycolic acid, glycerin stearate, glycerin monolaurate, glycerin monoalkyl ether, or any combinations thereof.

Aldehydes or aldehyde compositions containing an aldehyde selected from one class (Class A) and an aldehyde selected from a second class (Class B), have been found to have remarkable deodorant properties, clearly superior to those of each class of aldehyde compositions taken individually. The aldehyde technology consists of using materials of low vapor pressure. Efficacy is thought to be the result of a combination of various methods of neutralizing odors, which include, chemical reaction with malodorant molecules, slow evaporation of the functional ingredients, and a partial masking effect. In the presence of malodor, the reaction product has been chemically altered so that one of the following occurs: (1) the new molecule is more volatile and quickly evaporates, (2) the new molecule is much larger and virtually non-volatile so the nose cannot detect its presence, or (3) the new molecule, being chemically different, has a more pleasant odor profile.

Suitable Class A aldehydes, may include, for example, one or more acyclic aliphatic aldehydes, non-terpenic aliphatic aldehydes, non-terpenic alicyclic aldehydes, terpenic aldehydes, aliphatic aldehydes substituted by an aromatic group, bifunctional aldehydes, or any mixtures thereof. More specifically, suitable Class A aldehydes may include, for example, decanal, lilal, tripal, or any mixtures thereof.

Suitable Class B aldehydes may include, for example, one or more aldehydes having an unsaturation carried by the carbon in the alpha position of the aldehyde function, aldehydes having an unsaturation in the alpha position of the aldehyde function conjugated with an aromatic ring, aldehydes having the function carried by an aromatic ring, or any mixtures thereof. More specifically, suitable Class B aldehydes may include, for example, citral, benzaldehyde, vanillin, or any mixtures thereof.

The aldehyde compositions may contain three or more aldehydes, as long as each of the two classes are represented. Preferably, the aldehydes of Class A and Class B are present in a proportion of about 80/20 to about 20/80.

Natural oils may be used as a suitable odor absorbent material in the present invention. The natural oils can have the effect of suppressing the malodorant molecules and imparting a pleasant odor, which overpowers the malodor. By way of example, a suitable natural oil for use in the present invention is white cedar leaf oil.

Solutions of any soluble natural compounds capable of malodor counteraction may also be used in the present invention. One example of such a soluble natural compound is chlorophyll.

Natural plant and herb extracts may also be used as malodor counteractant materials in the present invention. By way of example, suitable natural extracts may include green tea extract, Glade® "Neutralizer" (proprietary mixture of plant and heb extracts), or any mixtures thereof.

Naturally occurring deodorizing active materials may also be used in the present invention to counteract malodors. Suitable naturally occurring deodorizing actives include, for example, farnesol, phenoxyethanol, alkali rhodanides, linalol, citronellol, geraniol, phenethyl alcohol, or any mixtures thereof.

One or more acids may be used as malodor counteractants that act to neutralize basic components of the malodor. Suitable acids include, for example, citric acid, acetic acid, other organic acids that are safe for use, or any mixtures thereof. Preferably, the acid is naturally sourced. The more preferred acid is citric acid. Preferably, the citric acid is naturally sourced.

One or more bases may be used as malodor counteractants that act to neutralize acid components of the malodor. Suitable bases include, for example, ammonia, tiethanolamine, or any mixtures thereof. Preferably, the one or more bases are naturally sourced and are in liquid form.

One or more oxidants that react with sulfide-containing compounds to reduce malodors may also be used in the present invention. By way of example, suitable oxidants may include ascorbic acid or other known oxidating materials. Preferably, the oxidant is ascorbic acid and, preferably, it is naturally sourced.

One or more chelating agents that react with any metal components and reduce or eliminate malodors may be used in the present invention. Suitable chelating agents may include, for example, ascorbic acid or other known chelating agents, such as, for example, EDTA. The preferred chelating agent is ascorbic acid. Also, preferably, the chelating agent is naturally sourced.

Certain esters having reactive double bonds have been found to have a quasi-universal ability of abating malodors. Suitable ester compounds for use in the present invention include, for example, NEUTROAIR® (a mixture of geranyl crotonate and dihexyl fumarate) or METAZENE® (lauryl methacrylate). Preferably, the ester is naturally sourced and is in liquid form.

Masking agents may be used as a malodor counteractant material in the present invention. Any agent capable of masking malodor may be used. However, typically, for example, a perfume or fragrance is used to mask or hide the malodor. Preferably, the masking agent is naturally sourced and is in liquid form.

Compounds that are capable of altering the body's sensory receptors may also be used in the present invention. Malodor counteractants share common areas of receptor sites with many known malodor-causing chemicals. Given sufficient concentration in the atmosphere, the malodor counteractants interact with the receptor proteins and render them unavailable to malodors. Therefore, without interaction of the malodor with the receptors, no perception of the malodor by the nose is possible. By way of example, Veilex® (proprietary ingredients), produced by BBA, is such a malodor counteractant suitable for use in the present invention. Preferably, the sensory receptor alterant malodor counteractants are naturally sourced and are in liquid form.

One or more oxidizing agents may be used as malodor counteractants that act to oxidize components of the malodor. Any suitable oxidizing agent may be used in the absorbent article of the present invention that are safe for use, such as, for example, hydrogen peroxide Preferably, the one or more oxidizing agents are in liquid form and are naturally sourced.

One or more biological agents may be used as malodor counteractants in the absorbent article of the present invention. Suitable biological agents include, for example, bacterial spores, enzymes, or any mixtures thereof. Preferably, the one or more biological agents are naturally sourced and are in liquid form.

One or more surfactants may be used as malodor counteractants in the absorbent article of the present invention. Suitable surfactants include, for example, anionic, nonionic, cationic, zwitterionic, silicone, or any mixtures thereof. Preferably, the one or more surfactants are naturally sourced and are in liquid form.

One or more surface active polymers may be used as malodor counteractants in the absorbent article of the present invention. Suitable surface active polymers include, for example, acrylate polymers. Preferably, the one or more surface active polymers are naturally sourced and in liquid form.

In one preferred embodiment of the present invention, the odor absorbent material is glycerin. The glycerin used is preferably USP grade glycerin. Since glycerin is a hygroscopic material, e.g., has a high affinity for water, it is thought that glycerin acts as an odor absorbent by attracting and retaining some odiferous gases. In addition, these gases may be dissolved in water that is attracted by the glycerin. The absorption of water into the glycerin also reduces the vapor pressure thereby reducing the amount of malodor.

The use of liquid glycerin has manufacturing advantages. For example, liquid glycerin is easier to apply than solid or semisolid materials, may be applied more uniformly, and applied over a larger surface area. In addition, the glycerin does not support microbial growth. Therefore, no additional methods are required to either reduce the microbial content of glycerin or maintain its reduced microbial level.

Due to the ease of application and the ability not to support microbial growth, glycerin is believed to have production cost advantages. Further, glycerin is less expensive than other known odor absorbent materials thereby providing even further cost savings or advantages. In a preferred embodiment of the present invention, the glycerin is used alone as the malodor counteractant material.

In a second embodiment of the present invention, the glycerin is used in conjunction with at least one additional malodor counteractant material that may further enhance the ability of the liquid glycerin to control odor. As stated above, and by way of example, suitable additional malodor counteractant materials may include: aldehydes, natural oils, solutions of soluble natural compounds, natural plant and herb extracts, naturally occurring deodorizing actives, acids, bases, oxidants, chelating agents, esters, masking agents, sensory receptor alterants, oxidizing agents, biological additives, surfactants, surface active polymers, zeolites, or any mixtures thereof.

The additional malodor counteractant materials added may be liquids or solids, however liquids are more preferable. The use of all naturally sourced materials for the malodor counteractant material system provides the advantage of all natural odor control.

The present invention, which does not support microbial growth, has the advantage of being able to insure that microbial limits are maintained. This may not be the case for water containing odor absorbent mixtures. This is an important aspect in the manufacture of feminine hygiene products. Specifically, this liquid malodor counteractant material system does not require additional steps to insure that microbial limits are maintained during processing, storage, application and any intermediate steps.

The one or more malodor counteractant materials may be added to any catamenial device. In the case of tampons, the malodor counteractant materials may be added to either the tampon or tampon pledget, or the tampon removal string. Adding the one or more malodor counteractant materials to the string may offer a benefit of improved deodorant protection since some of the malodor associated with tampons occurs in the vulva region due to oxidative processes and due to contamination by sweat, urine and fecal material.

The amount of malodor counteractant material should be the least amount necessary to counteract effectively the malodor. With respect to glycerin, it has been demonstrated by an in vitro odor absorbent efficacy study that the addition of as little as 0.05 grams (g) of glycerin is sufficient to absorb about 92% of a synthetic vaginal malodor. However, it is believed that in a super absorbency tampon or tampon pledget, the amount of glycerin is preferably about 0.01 grams to about 0.15 grams, and more preferably about 0.05 to about 0.15 grams. As discussed below, the amount of malodor counteractant material will vary for other types of fibrous devices.

Figure 2:
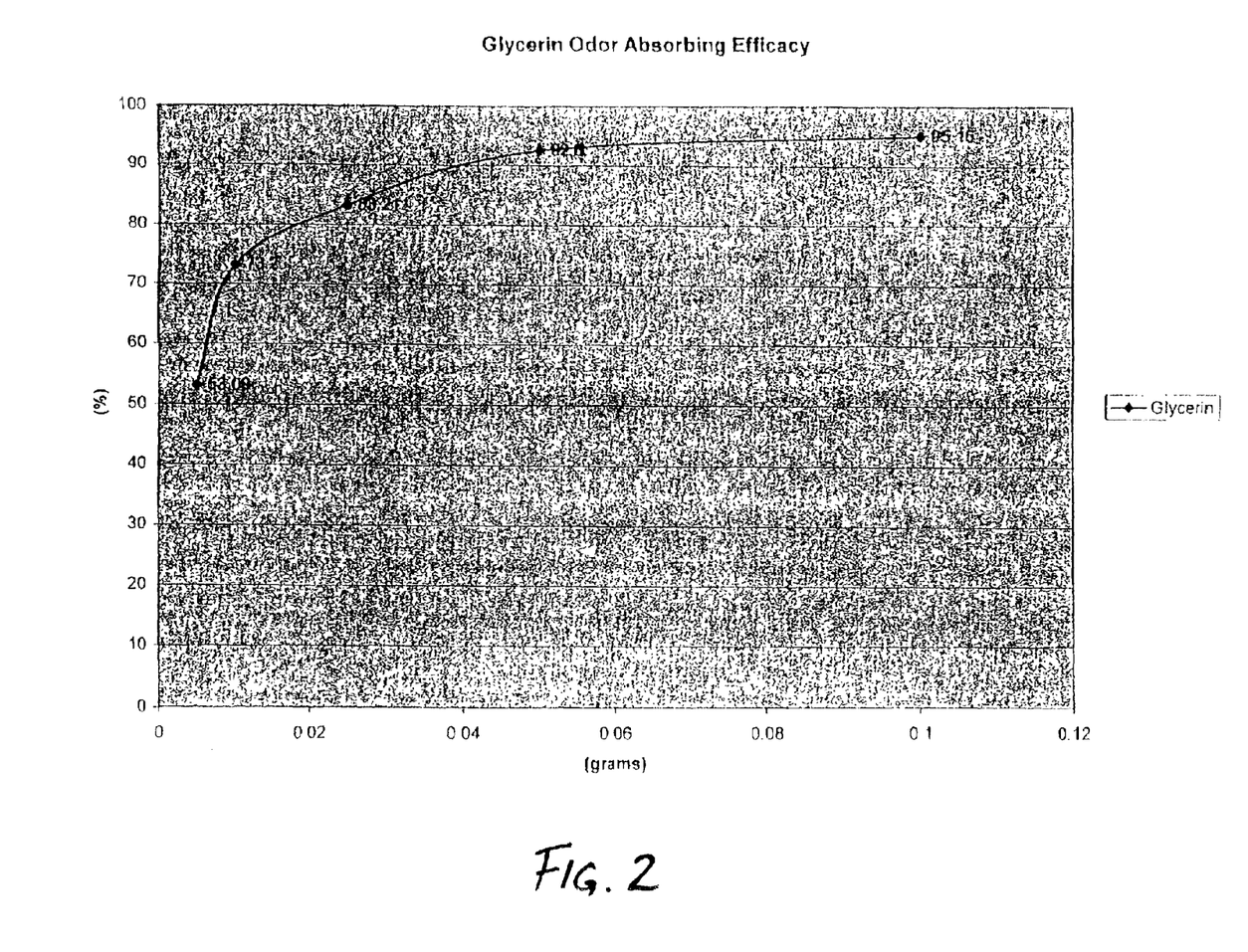
FIG. 2 is a chart of glycerin odor absorbing efficacy.
Figure 3:
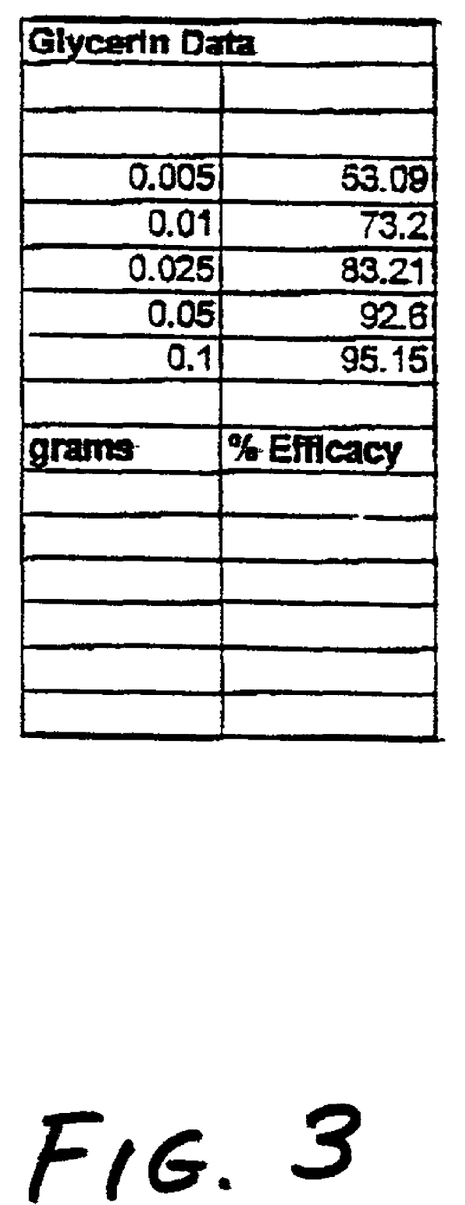
FIG. 3 is a summary of test results.

In vitro testing of malodor absorption determined by GC/headspace was conducted to determine the odor absorbent efficacy of the glycerin. This method used Gas Chromatograph/head space analysis to detect the presence of a known amount (2 μl.) of a synthetic vaginal malodor. Varying amounts of glycerin were introduced to the system. The amount of malodor absorbed by the test samples was determined. The glycerin was effective in absorbing or eliminating a synthetic vaginal malodor. About 0.05 grams of glycerin eliminated about 92% of a synthetic vaginal malodor. Using the same test method, it was shown, as demonstrated in FIG. 2, that as little as 0.01 grams absorbed 70% of the synthetic vaginal malodor. FIG. 3 is a summary of the test results.

As stated above, one embodiment of the present invention includes zeolite used in conjunction with the glycerin as the malodor counteractant materials. Preferably, the zeolite is a natural zeolite that is classified as either a thermal type 3 clinoptilolite species or chabasite species.

One zeolite useful in the present invention is designated CABSORB® ZK406H®, a product marketed by GSA Resources Inc. This material is in off-white clinoptilolite with potassium as the primary exchangeable cation. Potassium is present in an amount of the order of 4.3% of the zeolite. Another zeolite useful in the present invention is designated CABSORB® ZS500A®, a product marketed by GSA Resources Inc. This material is a tan mineral, chabasite, with sodium as the primary exchangeable cation. Sodium is present in an amount of the order of 6.7% of the zeolite.

The clinoptilolite species can also be characterized based on its chemistry and silica/alumina ratio, which is approximately 5.8:1. The following is a particular specification for the natural zeolite in the form of thermal type 3 clinoptilolite.

| CABSORB ® ZK406H ® Potassium Aluminosilicate Natural Clinoptilolite | |
|---|---|
| TYPICAL PROPERTIES | |
| Form | Granules |
| Color | Gray |
| Pore Diameter | 4.0 Angstroms |
| Pore Volume | 15% |
| Specific Surface Area | 40 m$^2$/g. |
| Bulk | 53-66 lbs/ft$^3$ |
| | 783-1054 Kg/m$^3$ |
| Solid Density | 87 lbs/ft$^3$ |
| | 1390 Kg/m$^3$ |
| Alkali Stability | pH of 7-10 |
| Acid Stability | pH of 3-7 |
| Thermal Stability | 1202 degrees F. |
| | 650 degrees C. |
| Ion Exchange Capacity | 1.65 milliequivalents/g |

| TYPICAL CHEMICAL ANALYSIS | | | | | | | |
|---|---|---|---|---|---|---|---|
| SiO$_2$ | Al$_2$O$_3$ | Fe$_2$O$_3$ | CaO | MgO | Na$_2$O | K$_2$O | MnO |
| 069.1 | 11.9 | 0.7 | 0.7 | 0.4 | 0.8 | 3.8 | 0.5 |

Besides potassium as the primary exchangeable cation, this particular zeolite has the following exchangeable cations:

| | | | | | | | | |
|---|---|---|---|---|---|---|---|---|
| Rb+ | Na+ | Ba+$^2$ | Mg+$^2$ | Li+ | Ag+ | Sr+$^2$ | Fe+$^3$ | K+ | Cd+$^2$ |
| Cu+$^2$ | Co+$^3$ | Cs+ | Pb+$^2$ | Ca+$^2$ | Al+$^3$ | NH4+ | Zn+$^2$ | Hg+$^2$ | Cr+$^3$ |

Of the above exchangeable cations, the amount of calcium, magnesium and sodium and their ratio to each other appears important. As set forth above, the amount of calcium (Ca) is 0.7, the amount of magnesium (Mg) is 0.4, and the amount of sodium (Na) is 0.8.

The chabasite species can be characterized based on its chemistry and silica/alumina ratio that is approximately 4:1. The following is a particular specification for the chabasite species.

| TYPICAL PROPERTIES | |
|---|---|
| Form | Powder or Granules |
| Color | Light Brown (Dry Brightness 43) |
| Ring Member | 8 |
| Crystal Size - Chabasite | Less than 1 micron |
| Crystallinity | +90% |
| Density | 1.73 g/cm$^3$ |
| Pore Size | 4.1 by 3.7 Angstroms |
| Effective Pore Diameter | 4.3 Angstroms |
| Cavity Size | 11.0 by 6.6 Angstroms |
| Total Pore Volume | .468 cm$^3$/g |
| Surface Area | 520.95 m$^2$/g |
| Crystal Void Volume | .47 cm$^3$/cm$^3$ |
| Packing Density | Approx. 577 kg/m$^3$ (36 lbs/ft$^3$) |
| SiO$_2$/Al$_2$O$_3$ Ratio | Approx. 4:1 |
| MOH's Hardness | 4-5 |
| Moisture as packaged | Less than 10% by weight |
| Stability | pH of 3 through 12 |
| Ion Exchange Capacity | 2.50 meq/g |

| TYPICAL CHEMICAL ANALYSIS (equilibrated at 20° C. and 40% relative humidity) | | | | | | | | |
|---|---|---|---|---|---|---|---|---|
| SiO$_2$ | Al$_2$O$_3$ | Fe$_2$O$_3$ | CaO | MgO | NaO | K2O | LOI | Dominant Cation |
| 54.6 | 14.9 | 2.28 | 0.22 | 0.60 | 6.67 | 0.90 | 19.4 | Na |

Exchange Selectivities $Tl^+ > Os^+ > K^+ > Ag^+ > Rb^+ > NH_4^+ > Pb^{2+} > Na^+ = Ba^{2+} > Sr^{2+} > Ca^{2+} > Li^+$ Exchange Of Heavy Metal Ions Weight Percent of Heavy Metals Retained in anhydrous CABSORB after Ion Exchange from a 0.10 mg/ml solution AgNO$_3$, Pb(NO$_3$)$_2$, CoSO$_4$ and a 0.025. mg/ml solution of CuSo$_4$ at the initial Mitial pH indicated for each solution.

| Ag | | Pb | | Cu | | Go | |
|---|---|---|---|---|---|---|---|
| pH | wt % | pH | wt % | pH | wt % | pH | wt % |
| 5.30 | 21.85 | 3.80 | 5.27 | 3.43 | 3.17 | 2.91 | 2.32 |

Figure 1:
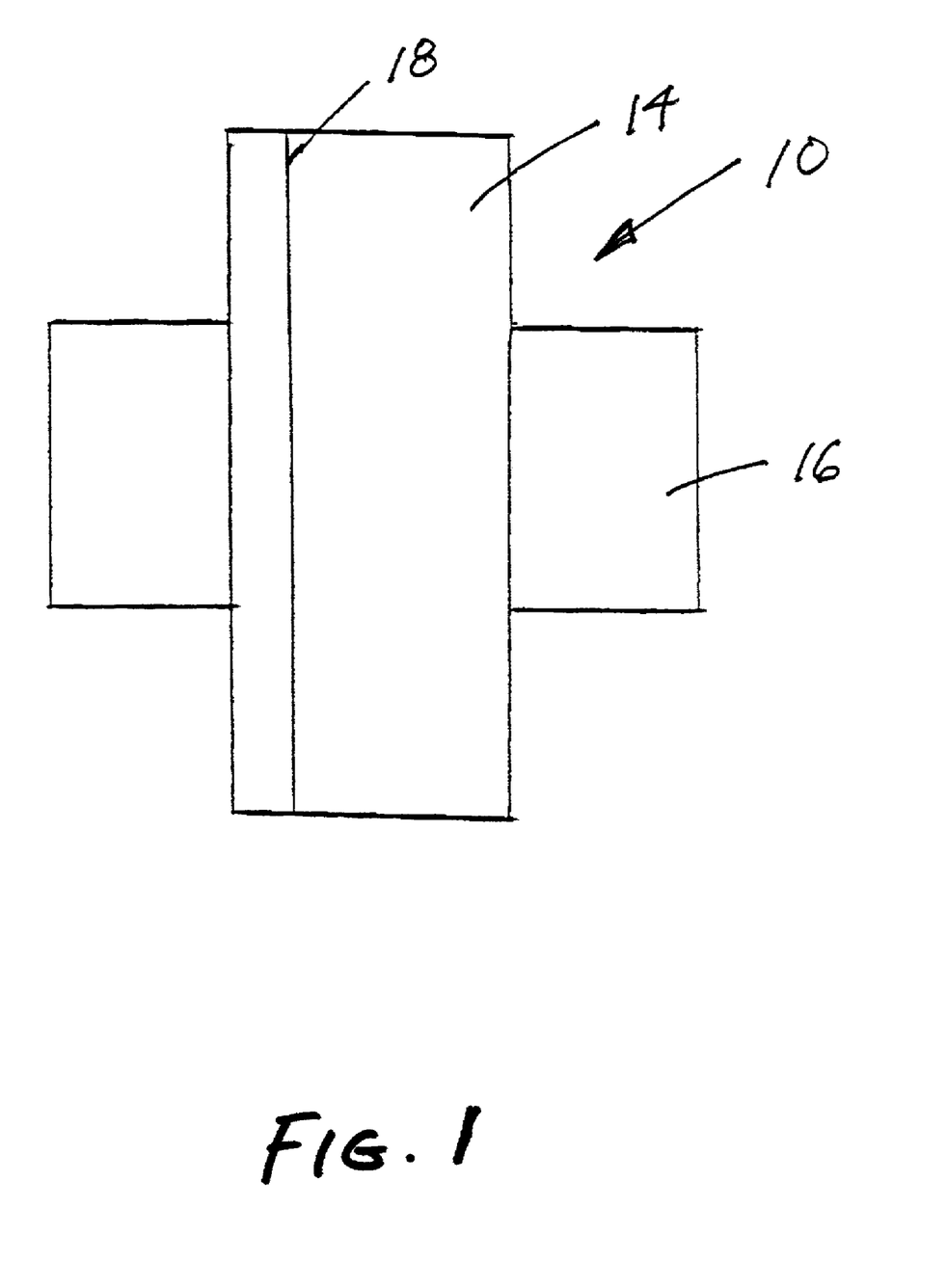
FIG. 1 is a top view of a cross-pad configuration for a tampon that incorporates the one or more malodor counteractant materials of the present invention.

In one embodiment of the present invention, as shown in FIG. 1, the fibrous absorbent article 10 comprises fibrous material capable of absorbing body fluids such as catamenial fluids and the like. The fibrous material may be arranged to form a woven or non-woven structure. Preferably, the fibrous absorbent article 10 of FIG. 1 is formed into a tampon. A tampon has a well-known final, cylindrical shape. However, a tampon may have a number of fibrous layers, such as inner layer 14 and outer layer 16, that are subsequently formed together into the cylindrical shaped tampon.

The one or more malodor counteractant materials 18 are disposed on or incorporated in the fibrous absorbent article 10. This incorporation may be accomplished within the structure between the layers 14 and 16 that form the tampon. The malodor counteractant materials 18 may also be incorporated in or on the absorbent article by one or more methods that include, for example, incorporating the counteractant into a fiber finish, blending it into the fibers or web, spraying it evenly over the inner and/or outer surfaces, or any combination thereof.

In one preferred embodiment of the present invention, the malodor counteractant materials 18 are placed continuously along the longitudinal extant of inner layer 14. In the more preferred embodiment, the one or more malodor counteractant materials 18 are placed in the centermost region of inner layer 14, however it or they are positioned just slightly-off center as shown in FIG. 1.

The amount of the malodor counteractant materials 18 applied to inner layer 14 should be sufficient to significantly reduce, if not essentially eliminate, the odors from the menstrual fluid. In the case of the tampon illustrated, as little as about 0.05 grams of glycerin has been found to effectively remove odors from a Super Absorbency tampon or tampon pledget having a weight of 2.6 grams fiber weight (excluding string).

The amount or amounts of malodor counteractant materials 18 used in the fibrous absorption article may vary depending upon the size of the tampon and, perhaps, cost considerations. However, it is believed that in a normal tampon, which includes playtex's presently sized slim, regular and super tampons, preferably about 0.01 grams to about 0.15 grams of malodor counteractant material should be used. More preferably, about 0.5 grams to about 0.1 grams should be used in a normal tampon. Although additional amounts above about 0.15 grams of glycerin could be used for odor absorption in a tampon, the additional amounts tend to interfere with other tampon properties of the tampon pledget. In other fibrous absorbing devices, the amount of malodor counteractant materials is preferably about 0.01 grams to about one-half the weight of the fibrous absorbent device. More preferably, the amount of malodor counteractant materials is about 0.1 grams to about 20% of the weight of the fibrous absorbent device.

The method of incorporating the one or more malodor counteractant materials into a tampon is important, as discussed above, since it provides a cost benefit. Basically, the one or more liquid malodor counteractant materials, preferably glycerin alone, is dispensed, as shown in FIG. 1, in a continuous line on the inner surface of inner layer 14 by a spreader or dispensing device or gun. As an alternative, it could be dispensed as individual droplets on the inner surface of inner layer 14 by a dispensing device or gun. The dispensing is by any conventional dispensing device or gun, such as, for example, a conventional glue-dispensing gun. This application also provides a uniform and even application throughout inner layer 14. The material may also be atomized or sprayed on the inner layer 14.

The present invention having been thus been described with particular reference to the preferred forms thereof, it will be obvious that various changes and modifications may be made therein without departing from the spirit and scope of the present invention as defined in the appended claims.

The invention claimed is:

1. A fibrous tampon for absorbing body fluids, the tampon comprising:
   at least one inner layer having one or more malodor counteractant materials incorporated therein; and
   at least one outer layer that along with said at least one inner layer forms a cross-pad configuration;
   wherein said one or more malodor counteractant materials is selected from the group consisting of: glycerin, glycerin compound, aldehyde, natural oil, solution of soluble natural compound, natural plant and herb extract, naturally occurring deodorizing active, citric acid, acetic acid, base, EDTA, ester, masking agent, sensory receptor alterant, oxidizing agent, biological agent, surfactant, surface active polymer, and any mixtures thereof;
   wherein said one or more malodor counteractant materials is present in an amount between about 0.01 grams to about 0.12 grams, and
   wherein said one or more malodor counteractant materials is in a liquid form.

2. The tampon of claim 1, wherein said one or more malodor counteractant materials is glycerin.

3. The tampon of claim 1, wherein said one or more malodor counteractant materials is present between about 0.1 grams to about 20% of the total weight of the tampon.

4. A fibrous tampon for absorbing body fluids, the tampon comprising:
   at least one inner layer having liquid glycerin incorporated therein; and
   at least one outer layer that along with said at least one inner layer forms a cross-pad configuration;
   wherein said liquid glycerin is present in an amount between about 0.01 grams to about 0.05 grams, and
   wherein said liquid glycerin is naturally sourced.

5. The tampon of claim 4, further comprising one or more additional malodor counteractants selected from the group consisting of: aldehyde, natural oil, solution of soluble natural compound, natural plant and herb extract, naturally occurring deodorizing active, acid, base, oxidant, chelating agent, ester, masking agent, sensory receptor alterant, oxidizing agent, biological agent, surfactant, surface active polymer, and any mixtures thereof.

6. A fibrous tampon for absorbing body fluids comprising:
   a fibrous article having at least one inner layer and at least one outer layer suitable for absorbing said body fluids; and
   a liquid glycerin that does not support microbial growth, disposed continuously along a longitudinal extant of said at least one inner layer to absorb odors associated with said body fluids, wherein said liquid glycerin is present in an amount between about 0.01 grams to about 0.12 grams.

7. The tampon of claim 6, wherein said liquid glycerin is combined with at least one additional malodor counteractant material selected from the group consisting of: aldehyde, natural oil, solution of soluble natural compound, natural plant and herb extract, naturally occurring deodorizing active, acid, base, oxidant, chelating agent, ester, masking agent, sensory receptor alterant, oxidizing agent, biological agent, surfactant, surface active polymer, zeolite, and any mixtures thereof.

8. The tampon of claim 7, wherein said one additional malodor counteractant material is naturally sourced.

9. The tampon of claim 6, wherein said liquid glycerin is naturally sourced.

10. A method of deodorizing a vaginal area comprising:
    applying to said vaginal area a multi-layered fibrous absorbent article having a malodor counteractant material comprising:
    glycerin; and
    at least one additional malodor counteractant material selected from the group consisting of: aldehyde, natural oil, solution of soluble natural compound, natural plant and herb extract, naturally occurring deodorizing active, citric acid, base, EDTA, ester, masking agent, sensory receptor alterant, oxidizing agent, biological agent, surfactant, surface active polymer, zeolite, and any mixtures thereof,
    wherein said glycerin and said at least one additional malodor counteractant material counteracts malodor in said vaginal area, wherein said multi-layered fibrous absorbent article has an inner layer and an outer layer, said inner layer along with said outer layer forming a cross-pad configuration,
    wherein said glycerin and said at least one additional malodor counteractant material are incorporated in said multi-layered fibrous absorbent article between said inner layer and said outer layer, and
    wherein said malodor counteractant material is present in an amount of about 0.01 grams to about 0.12 grams.

11. The method of claim 10, wherein said malodor counteractant material is present in an amount of about 0.01 grams to about 0.05 grams.

12. A method of deodorizing a vaginal area comprising:
    applying to said vaginal area a fibrous absorbent article having a fibrous material suitable for absorbing body fluids and a liquid glycerin that does not support microbial growth disposed in said fibrous material, wherein said liquid glycerin is present in an amount between about 0.01 grams to about 0.05 grams, wherein said fibrous absorbent article has at least one inner layer and at least one outer layer, wherein said liquid glycerin is disposed on said fibrous absorbent article, and wherein said liquid glycerin counteracts malodor in said vaginal area.

13. The method of claim 12, wherein said at least one inner layer and said at least one outer layer form a cross-pad configuration.

* * * * *